United States Patent
Heaton et al.

(10) Patent No.: US 6,756,407 B2
(45) Date of Patent: Jun. 29, 2004

(54) METHOD AND COMPOSITIONS FOR THE TREATMENT OR AMELIORATION OF FEMALE SEXUAL DYSFUNCTION

(75) Inventors: Jeremy P. W. Heaton, Gananoque (CA); Michael A. Adams, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 10/126,933

(22) Filed: Apr. 22, 2002

(65) Prior Publication Data

US 2002/0193442 A1 Dec. 19, 2002

Related U.S. Application Data

(60) Division of application No. 09/336,088, filed on Jun. 18, 1999, now Pat. No. 6,395,744, which is a continuation-in-part of application No. 09/102,987, filed on Jun. 22, 1998.

(51) Int. Cl.[7] .................. A61K 31/19; A61K 31/557
(52) U.S. Cl. ................... 514/573; 514/284; 514/772.6
(58) Field of Search ............................ 514/284, 573, 514/772.6

(56) References Cited

U.S. PATENT DOCUMENTS

| | | | |
|---|---|---|---|
| 2,818,855 A | 1/1958 | Miller | 128/79 |
| 4,127,118 A | 11/1978 | Latorre | 128/79 |
| 4,521,421 A | 6/1985 | Foreman | 514/267 |
| 4,521,521 A | 6/1985 | Abbott et al. | 436/517 |
| 4,543,256 A | 9/1985 | Neumeyer | 514/280 |
| 4,687,773 A | 8/1987 | Neumeyer et al. | 514/280 |
| 4,727,064 A | 2/1988 | Pitha | 514/58 |
| 4,801,587 A | 1/1989 | Voss et al. | 514/248 |
| 5,242,391 A | 9/1993 | Place et al. | 604/60 |
| 5,270,323 A | 12/1993 | Milne, Jr. et al. | 514/309 |
| 5,770,606 A | 6/1998 | El-Rashidy et al. | 514/284 |

(List continued on next page.)

FOREIGN PATENT DOCUMENTS

| | | | |
|---|---|---|---|
| EP | 0 172 697 A2 | 2/1986 | A61K/31/435 |
| EP | 0 579 435 A1 | 1/1994 | A61K/47/48 |
| WO | WO 87/04621 | 8/1987 | A61K/31/50 |
| WO | WO 93/23035 | 11/1993 | A61K/31/40 |
| WO | WO 94/22445 | 10/1994 | A61K/31/48 |

OTHER PUBLICATIONS

Davis, SR, "The role of androgens and the menopause in the female sexual response", in *International Journal of Impotence Research* (1998 Stockton Press) vol. 10, Suppl. 2, S82–S83.*

(List continued on next page.)

*Primary Examiner*—Thurman K. Page
*Assistant Examiner*—Konata M. George
(74) *Attorney, Agent, or Firm*—Stephen J. Scribner; Carol Miernicki Steeg

(57) ABSTRACT

The present invention provide a method of treating sexual dysfunction in a female, including the vasculogenic symptoms of delayed vaginal engorgement, diminished vaginal lubrication, pain or discomfort with intercourse (dyspareunia), diminished vaginal sensation, diminished vaginal orgasm, diminished clitoral sensation or diminished clitoral orgasm, or of combating vaginal pain by stimulating peripheral pelvic nerve release of nitric oxide (NO). The method comprises administering to a female in need of such treatment a therapeutically effective amount of a compound which acts on a mid-brain pathway to increase blood flow to the ilio-hypogastric-pudendal artery bed and stimulate the release of nitric oxide (NO) from peripheral NANC nerve cells. The preferred compound for the method of this invention is apomorphine or one of its pharmaceutically acceptable salts, esters, or pro-drugs. Alternatively, the apomorphine is co-administered with an apomorphine-potentiating amount of an androgen, preferably testosterone either prior to, or concomitantly with, the administration of the apomorphine.

19 Claims, 10 Drawing Sheets

U.S. PATENT DOCUMENTS

| | | | | |
|---|---|---|---|---|
| 5,945,117 A | * | 8/1999 | El-Rashidy et al. | 424/430 |
| 6,395,744 B1 | * | 5/2002 | Adams et al. | 514/284 |
| 6,403,605 B1 | | 6/2002 | Heaton et al. | |

OTHER PUBLICATIONS

Derogatis, LR and B Conklin–Powers, "Psychological assessment measures of female sexual functioning in clinical trials", in *International Journal of Impotence Research* (1998 Stockton Press) vol. 10, Suppl. 2, S111–116.*

Fourcroy, Jean, "Discussion: Female sexual function—mechanisms and models", in *International Journal of Impotence Research* (1998 Stockton Press) vol. 10, Suppl. 2, S98–S101.*

Fourcroy, JL, "Issues and priorities in the development of drug treatments for female sexual dysfunction", in *International Journal of Impotence Research* (1998 Stockton Press) vol. 10, Suppl. 2, S121–S123.*

Goldstein, I, and Berman, JR, "Vasculogenic female sexual dysfunction: vaginal engorgement and clitoral erectile insufficiency syndromes", in *International Journal of Impotence Research* (1998 Stockton Press) vol. 10, Suppl. 2, S84–S90.*

Harvard Scientific Corp., *Harvard Scientific Acquires Rights to Oral Treatment for Both Male & Female Sexual Dysfunction* pp. 1–3, (Jun. 12, 1998). (Downloaded from the Internet at http://biz.yahoo.com/.)

Heiman, JR, "Psychophysiological models of female sexual response", in *International Journal of Impotence Research* (1998 Stockton Press) vol. 10, Suppl. 2, S94–S97.*

Laan, E and Everaerd, W, "Physiological measures of vaginal vasocongestion", in *International Journal of Impotence Research* (1998 Stockton Press) vol. 10, Suppl. 2, S107–S110.*

Leiblum, SR, "Definition and classification of female sexual discorders", in *International Journal of Impotence Research* (1998 Stockton Press) vol. 10, Suppl. 2, S104–S106.*

Phillips, NA, "The clinical evaluation of dyspareunia", in *International Journal of Impotence Research* (1998 Stockton Press) vol. 10, Suppl. 2, S117–S120.*

Sarrel, PM, "Ovarian hormones and vaginal blood flow: using laser Doppler velocimetry to measure effects in a clinical trial of post–menopausal women", in *International Journal of Impotence Research* (1998 Stockton Press) vol. 10, Suppl. 2, S91–S93.*

*This information was first presented at the Cape Cod Conference of May 20–31, 1997. The references were first published in the United Kingdom on Feb. 6, 1998 and distributed for overseas publication on May 6, 1998.

PubMed/NCBI abstract, accessed Aug. 27, 2001, for: Davis, S.R., "The clinical use of androgens in female sexual disorders," *J. Sex. Marital Ther.* 24:153–163, Brunner–Routledge (Jul.–Sep. 1998).

PubMed/NCBI abstract, accessed Aug. 27, 2001, for: Kennedy, R.G. et al., "Sexual interest in postmenopausal women is related to 5alpha–reductase activity," *Hum. Reprod.* 12:209–213, Oxford University Press, HighWire Press and The European Society of Human Reproduction and Embryology (Feb. 1997).

PubMed/NCBI abstract, accessed Sep. 24, 2001, for: Kirchengast, S. et al., "Decreased sexual interest and its relationship to body build in postmenopausal women," *Maturitas* 23:63–71, European Menopause and Andropause Society (EMAS) and Elsevier Science Ltd. (Feb. 1996).

Lloyd, R.V. and Fields, K.L., "Regulation of dopamine receptors in the MtT/W15 transplantable pituitary tumor by estrogen," *Mol. Cell. Endocrinol.* 44:133–139, Elsevier Scientific Publishers Ireland, Ltd. (1986).

PubMed/NCBI abstract, accessed Aug. 27, 2001, for: Mathews, A., "Progress in the treatment of female sexual dysfunction," *J. Psychosom. Res.* 27:165–173, Elsevier Science Ltd. (1983).

PubMed/NCBI abstract, accessed Aug. 27, 2001, for: Tutten, A. et al., "Discrepancies between genital responses and subjective sexual function during testosterone substitution in women with hypothalamic amenorrhea," *Psychosom. Med.* 58:234–241, American Psychosomatic Society (May–Jun. 1996).

Ferrari, F. et al., Influence of Apomorphine on Rat Female Sexual Behaviour and its Relation with Induction of Stereotypy, *Rivista di Farmacologia e Terapia VIII*, pp. 355–363 (1977).

Melis, Maria Rosaria et al., Dopamine and Sexual Behaviour, *Neuroscience and Biobehavioral Reviews*, vol. 19, No. 1, pp. 19–38 (1995).

Segraves, R. T. et al., Pharmacotherapy for Sexual Disorders: Advantages and Pitfalls, *Sexual and Marital Therapy*, vol. 13, No. 3, pp. 295–309 (1998).

Tagliamonte et al., Pharm. Biochem. and Behavior vol. 2, pp. 257–260 (1974).

Laduron et al., Biochem. Pharmacology, vol. 28, pp. 2161–2165 (1979).

Baldessarini et al., in Gessa et al., Apomorphine & Other Dopaminomimetics, vol. 1, Basic Pharmacology, pp. 219–288 (1981).

Lal et al., J. Neural Transmission, vol. 54, pp. 75–84 (1982).

Reynolds, James E. F., ed., Martindale, 28th Edition, pp. 891–892 (1982).

Gower et al., European J. of Pharmacology, vol. 122, pp. 239–244 (1986).

Melis et al., Brain Research, vol. 415, 98–104 (1987).

Segraves et al., Archives of Sexual Behavior, vol. 16, No. 2, pp. 125–137 (1987).

Danjou et al., Br. J. Clin. Pharmac., vol. 26, pp. 733–739 (1988).

Lal S., Prog. Neuro–Psychopharm. & Biol. Psych., vol. 12, pp. 117–164 (1988).

Pehek et al., Pharm. Biochem. and Behavior 31:201–208 (1988).

Danjou et al., J. Pharmacol. Methods, vol. 21, pp. 61–69 (1989).

Gancher et al., Am. Neurol., vol. 26, pp. 232–238 (1989).

Segraves R. T., Arch. Gen. Psych., vol. 46, pp. 275–284 (1989).

Durif et al., Eur. J. Clin. Pharmacology, vol. 41, pp. 493–494 (1991).

Essink et al., J. Chromatography, vol., 570, pp. 419–424 (1991).

Gancher et al., Movement Disorders, vol. 6, No. 3, pp. 212–216 (1991).

Heaton et al., J. Urology, vol. 145, pp. 192–194 (1991).

Heaton et al., J. Urology, vol. 145 pp. 1099–1102 (1991).

Lal et al., J. Psych. Neurosci., vol. 16, No. 5, pp. 262–266 (1991).

Montastruc et al., Clin. Neuropharmacology, vol. 14, No. 5, pp. 432–437 (1991).

Panegyres et al., Med. J. Australia, vol. 155, pp. 371–374 (1991).

Segraves et al., J. Urology, vol. 145, pp. 1174–1175 (1991).

Durif et al., Clinical Neuropharmacology, vol. 16, No. 2, pp. 157–166 (1993).

Heaton et al., J. Urology, vol. 151, pp. 797–800 (1994).

Bancroft, J., editor, The Pharmacology of Sexual Function and Dysfunction, pp. 225–229 (1995).

Goodman and Gilman, eds., The Pharmacological Basis of Therapeutics, 9th Edition, pp. 4–9 (1996).

Hamburger–Bar, Rachel, et al, "Apomorphine: Facilitation of Sexual Behaviour in Female Rats", *European Journal of Pharmacology*, vol. 32, pp. 357–360 (1975).

Hruska, Robert E., and E.K. Silbergeld, "Estrogen Treatment Enhances Dopamine Receptor Sensitivity in the Rat Striatum", *European Journal of Pharmacology*, vol. 61, pp. 397–400 (1980).

Bancroft, M.D., "Hormones and Human Sexual Behavior", *Journal of Sex & Marital Therapy*, vol. 10, No. 1, pp. 3–19 (1984).

Fernandez–Guasti, A., et al., "Separation of Dopaminergic and Serotonergic Inhabitory Mechanisms in the Mediation of Estrogen–Induced Lordosis Behaviour in the Rat", *Pharmacol Biochem Behav* 27(1), pp. 93–98, (1987).

Kazandjian, A. et al., "Apomorphine–induced Behaviour During the Oestrous Cycle of the Rat", *Neuropharmacology*, vol. 26, No. 8, pp. 1037–1045 (1987).

Kaplan, Helen Singer and Trude Owett, "The Female Androgen Deficiency Syndrome", *Journal of Sex & Marital Therapy*, vol. 19, No. 1, Spring, pp. 3–21 (1993).

Meston, Cindy M., and Boris B. Gorzalka, "Differential Effects of Sympathetic Activation on Sexual Arousal in Sexually Dysfunctional and Functional Women", *Journal of Abnormal Psychology*, vol. 105, No. 4, pp. 582–591(1996).

Whipple, Beverly, et al., "Sexual Response to Self–stimulation in Women With Complete Spinal Cord Injury", *The Journal of Sex Research*, vol. 33, No. 3, pp. 231–240 (1996).

Komisaruk, Barry R., et al., "'Complete' Spinal Cord Injury Does Not Block perceptual responses to Genital Self–stimulation in Women", *Archives of Neurology*, vol. 54, pp. 1513–1520 (1997).

Meston, Cindy M., PhD, et al., "Inhibition of Subjective and Physiological Sexual Arousal in Women by Clonidine", *Psychosomatic Medicine*, vol. 59, pp. 399–407 (1997).

Berman, Jennifer R., et al., "Effect of Estrogen Withdrawal on Nitric Oxide Synthase Expression and Apoptosis in the Rat Vagina", *Urology*, vol. 51(4), pp. 650–656 (1998).

Meston, Cindy M., PhD, and Julia R. Heiman, PhD, "Ephedrine–Activated Physiological Sexual Arousal in Women", *Arch Gen Psychiatry*, vol. 55, pp. 652–656 (Jul. 1998).

Azadzoi, Kazem, M.D., "Arterial Insufficiency and Femal Sexual Dysfunction".**

Fleming, Sandra, "Arteriogram Studies in Women with Peripheral Vascular Disease".**

Leiblum, Sandra, Ph.D., "Classification of Femal Sexual Dysfunctions: Issues and Controversies".**

Redmond, Geoffrey, M.D., "Testosterone and Female Sexual Dysfunction".**

Weiss, Robert M., M.D., "Estrogen Deficiency and Female Sexual Dysfunction".**

Azadzoi, Kazem M., et al., "Mechanism of clitoral cavernosal and vaginal tissue contractility in the rabbit", 94th Annual Meeting, American Urological Association,(May 1999).

**This information was published as material for a course offered by Boston University School of Medicine and Department of Urology on Oct. 23–25, 1998. The course was entitled "New Perspectives In the Management of Female Sexual Dysfunction".

Ferrari, F. et al., Influence of Apomorphine on Rat Female Sexual Behaviour and its Relation with Induction of Stereotypy, *Rivista di Farmacologia e Terapia VIII*, pp. 355–363 (1977).

Melis, Maria Rosaria et al., Dopamine and Sexual Behavior, *Neuroscience and Biobehavioral Reviews*, vol. 19, No. 1, pp. 19–38 (1995).

Tagliamonte et al., "Possible Stimulatory Role of Brain Dopamine in the Copulatory Behavior of Male Rats", Pharmacology Biochemistry and Behavior, vol. 2, pp. 257–260(1974).

Hamburger–Bar, Rachel et al, "Apomorphine: Facilitation of Sexual Behaviour in Female Rats", European Journal of Pharmacology, vol. 32, pp. 357–360(1975).

Database CaPlus, DN 92:70106. Soulairac, A. Sex. Endocrinol.: Horm. Relat. Physiopathol. Pregnancy, Horm. Invest., Hypothal.–Hyophyseal Relat., [Proc. Symp. Fond. Rech. Endocrinol. Sex. Reprod. Hum.], 4th (1978), Meeting Date 1976, 153–74. Edi.

Foreman, Mark M., et al., "Role of Hypothalamic Dopaminergic Receptors in the Control of Lordosis Behavior in the Female Rat", Physiology & Behavior, vol. 23, pp. 283–289 (1979).

Laduron et al., "Domperidone, A Specific In Vitro Dopamine Antagonist, Devoid of In Vivo Central Dopaminergic Activity", Biochemical Pharmacology, vol. 28, pp. 2161–2165 (1979).

Hruska, Robert E., and E.K. Silbergeld, "Estrogen Treatment Enhances Dopamine Receptor Sensitivity in the Rat Striatum", European Journal of Pharmacology, vol. 61, pp. 397–400 (1980).

Baldessarini, R.J. et al., "Preclinical Studies of the Pharmacology of Aporphines", G.L. Gessa et al., eds., Apomorphine & Other Dopaminomimetics, vol. 1: Basic Pharmacology, Raven Press, N.Y. pp. 219–228 (1981).

Lal et al., "Effect of Domperidone on Apomorphine–Induced Growth Hormone Secretion in Normal Men", Journal of Neural Transmission, vol. 54, pp. 75–84(1982).

Reynolds, James E. F., Ed., Martindale, "The Extra Pharmacopoeia 28th Edition", The Pharmaceutical Press, London. pp. 891–892(1982).

Bancroft, M.D., "Hormones and Human Sexual Behavior", Journal of Sex & Marital Therapy, vol. 10, No. 1, pp. 3–19(1984).

Gower et al., "Antagonism of Drug–Induced Yawning and Penile Erections in Rats", European Journal of Pharmacology, vol. 122, pp. 239–244(1986).

Fernandez–Guasti, A., et al., "Separation of Dopaminergic and Serotonergic Inhabitory Mechanisms in the Mediation of Estrogen–Induced Lordosis Behaviour in the Rat", Pharmacol Biochem Behav 27(1), pp. 93–98, (1987).

Kazandjian, A. et al., "Apomorphine–induced Behaviour During the Oestrous Cycle of the Rat", Neuropharmacology, vol. 26, No. 8, pp. 1037–1045(1987).

Melis, Maria Rosaria, et al., "Apomorphine–induced penile erection and yawning: siste of action in brain", Brain Research, vol. 415, pp. 98–104(1987).

Segraves, K.A. et al., "Use of Sexual History to Differentiate Organic from Psychogenic Impotence", Archives of Sexual Behavior, vol. 16(2), pp. 125–137(1987).

Danjou et al., "Assessment of erectogenic properties of apomorphine and yohimbine in man", Br. J. Clin. Pharmac., vol. 26, pp. 733–739(1988).

Lal, Samarthji, "Apomorphine in the Evaluation of Dopaminergic Function in Man", Prog. Neuro–Psychopharmacol. & Biol. Psychiat. vol. 12, pp. 117–164(1988).

Pehek et al., "Apomorphine and Haloperidon, but not Domperidone, affect Penile Reflexes in Rats", Pharmacology Biochemistry & Behavior, vol. 31, pp. 201–208(1988).

Danjou, P., et al., "Assessment of Erectogenic Drugs by numeric Plethysmography", Journal of Pharmacological Methods, vol. 21, pp. 61–69(1989).

Gancher et al., "Peripheral Pharmacokinetics of Apomorphine in Humans", Am. Neurol Assoc., vol. 26, pp. 232–238(1989).

Segraves, R. Taylor, "Effects of Psychotropic Drugs on Human Erection and Ejaculation", Arch. Gen. Psychiatry, vol. 46, pp. 275–284 (1989).

Durif, F., et al., "Relation between plasma concentration and clinical efficacy after sublingual single dose apomorphine in Parkinson's disease", European Journal of Clinical Pharmacology., vol. 41, pp. 493–494 (1991).

Essink, A.W.G., et al., "Selective and quantitative isolation and determination of apomorphine in human plasma", Journal of Chromatography, vol. 570, pp. 419–424(1991).

Gancher, Stephen T., et al., "Absorption of Apomorphine by Various Routes in Parkinsonism", Movement Disorders, vol. 6(3), pp. 212–216 (1991).

Heaton, J.P.W., and S. Varrin, "The Impact of Alcohol Ingestion on Erections in Rats as Measured by a Novel Bio–assay", The Journal of Urology, vol. 145, pp. 192–194(1991).

Heaton, Jeremy P.W., et al., "The Characterization of a Bio–assay of Erectile Function in a Rat Model", The Journal of Urology, vol. 145, pp. 1099–1102(1991).

Lal, S., et al., "Effect of Bromocriptine in Patients With Apomorphine–Responsive Erectile Impotence: An Open Study", J. Psychiatr. Neurosci., vol. 16(5), pp. 262–266(1991).

Levin, R.J., "VIP, Vagina, clitoral and Periurethral Glans— an Update of Human Female Genital Arousal", Exp. Clin. Endocrinol., vol. 98, No. 2, pp. 61–69(1991).

Montastruc, J.L., et al., "Sublingual Apomorphine in Parkinson's Disease: A clinical and Pharmacokietic Study", Clinical Neuropharmacology, vol. 14(5), pp. 432–437(1991).

Panegyres, Peter K., et al., "Sublingual apomorphine solution in Parkinson's disease", The Medical Journal of Australia, vol. 155, pp. 371–374(1991).

Segraves, R.T., et al., "Effect of Apomorphine on Penile Tumescence in Men with Psychogenic Impotence", The Journal of Urology, vol. 145, pp. 1174–1175(1991).

Database MEDLINE, DN 92217484. Bertschy et al. Encephale, 17(6) 515–7(Nov. 1991).

Durif, F., et al., "Relation Between Clinical Efficacy and Pharmacokinetic Parameters After Sublingual Apomorphine in Parkinson's Disease", Clinical Neuropharmacology, vol. 16(2), pp. 157–166(1993).

Kaplan, Helen Singer and Trude Owett, "The Female Androgen Deficiency Syndrome", Journal of Sex & Marital Therapy, vol. 19, No. 1, Spring, pp. 3–21(1993).

Heaton, Jeremy P.W. and Shawn J. Varrin, Effects of Castration and Exogenous Testosterone Supplementation in an Animal Model of Penile Erection, The Journal of Urology, vol. 151, pp. 797–800(1994).

Bancroft, J., editor, The Pharmacology of Sexual Function and Dysfunction, Excerpta Medica, Amsterdam, pp. 225–229 (1995).

Goodman and Gilman, eds., The Pharmacological Basis of Therapeutics, 9th Edition, McGraw–Hill, New York, N.Y., pp. 4–9(1996).

Meston, Cindy M., and Boris B. Gorzalka, "Differential Effects of Sympathetic Activation on Sexual Arousal in Sexually Dysfunctional and Functional Women", Journal of Abnormal Psychology, vol. 105, No. 4, pp. 582–591(1996).

Whipple, Beverly, et al., "Sexual Response to Self–stimulation in Women With complete Spinal Cord Injury", The Journal of Sex Research, vol. 33., No. 3, pp. 231–240(1996).

Komisaruk, Barry R., et al., "'Complete' Spinal Cord Injury Does Not Block perceptual responses to Genital Self–stimulation in Women", Archives of Neurology, vol. 54, pp. 1513–1520(1997).

Meston, Cindy M., PhD, et al., "Inhibition of Subjective and Physiological Sexual Arousal in Women by Clonidine", Psychosomatic Medicine, vol. 59, pp. 399–407(1997).

Berman, Jennifer R., et al., "Effect of Estrogen Withdrawal on Nitric Oxide Synthase Expression and Apoptosis in the Rat Vagina", Urology, vol. 51(4), pp. 650–656(1998).

Davis, SR, "The role of androgens and the menopause in the female sexual response", in International Journal of Impotence Research (1998 Stockton Press) vol. 10, Suppl. 2, S82–S83.*

Derogatis, LR and B Conklin–Powers, "Psychological assessment measures of female sexual functioning in clinical trials", in International Journal of Impotence Research (1998 Stockton Press) vol. 10, Suppl. 2, S111–116.*

Fourcroy, Jean, "Discussion: Female sexual function— mechanisms and models", in International Journal of Impotence Research (1998 Stockton Press) vol. 10, Suppl. 2, S98–S101.*

Fourcroy, JL, "Issues and priorities in the development of drug treatments for female sexual dysfunction", in International Journal of Impotence Research (1998 Stockton Press) vol. 10, Suppl. 2, S121–S123.*

Goldstein, I, and Berman, JR, "Vasculogenic female sexual dysfunction: vaginal engorgement and clitoral erectile insufficiency syndromes" in International Journal of Impotence Research (1998 Stockton Press) vol. 10, Suppl. 2, S84–S90.*

Harvard Scientific Corp., Harvard Scientific Acquires Rights to Oral Treatment for Both Male & Female Sexual Dysfunction, pp. 1–3, (Jun. 12, 1998). (Downloaded from the Internet at http://biz.yahoo.com/.).

Heiman, JR, "Psychophysiological models of female sexual response", in International Journal of Impotence Research (1998 Stockton Press) vol. 10, Suppl. 2, S94–S97.*

Laan, E and Everaerd, W, "Physiological measures of vaginal vasocongestion", in International Journal of Impotence Research (1998 Stockton Press) vol. 10, Suppl. 2, S107–S110.*

Leiblum, SR, "Definition and classification of female sexual disorders", in International Journal of Impotence Research (1998 Stockton Press) vol. 10, Suppl. 2, S104–S106.*

Phillips, NA, "The clinical evaluation of dyspareunia", in International Journal of Impotence Research (1998 Stockton Press) vol. 10, Suppl. 2, S117–S120.*

Sarrel, PM, "Ovarian hormones and vaginal blood flow: using laser Doppler velocimetry to measure effects in a clinical trial of post–menopausal women", in International Journal of Impotence Research (1998 Stockton Press) vol. 10, Suppl. 2, S91–S93.*

Meston, Cindy M., PhD, and Julia R. Heiman, PhD, "Ephedrine–Activated Physiological Sexual Arousal in Women", Arch Gen Psychiatry, vol. 55, pp. 652–656 (Jul. 1998).

Azadzoi, Kazem, M.D., "Arterial Insufficiency and Female Sexual Dysfunction".**

Fleming, Sandra, "Arteriogram Studies in Women with Peripheral Vascular Disease".**

Leiblum, Sandra, Ph.D., "Classification of Female Sexual Dysfunctions: Issues and Controversies".**

Redmond, Geoffrey, M.D., "Testosterone and Female Sexual Dysfunction".**

Weiss, Robert M., M.D., "Estrogen Deficiency and Female Sexual Dysfunction".**

Azadzoi, Kazem M., et al., "Mechanism of clitoral cavernosal and vaginal tissue contractility in the rabbit", 94th Annual Meeting, American Urological Association,(May 1999).

*This information was first presented at the Cape Cod Conference May 20–31, 1997. The references were first published in the United Kingdom on Feb. 6, 1998 and distributed for overseas publication on May 6, 1998.

** This information was published as material for a course offered by Boston University School of Medicine and Department of Urology on Oct. 23–25, 1998. The course was entitled "New Perspectives In the Management of Female Sexual Dysfunction".

* cited by examiner

METHOD AND COMPOSITIONS FOR THE TREATMENT OR AMELIORATION OF FEMALE SEXUAL DYSFUNCTION

CROSS-REFERENCE TO RELATED APPLICATIONS

This application is a division of application Ser. No. 09/336,088, filed on Jun. 18, 1999, now U.S. Pat. No. 6,395,744, which is a continuation-in-part of co-pending application Ser. No. 09/102,987, filed on Jun. 22, 1998.

FIELD OF THE INVENTION

The present invention relates to methods of diagnosing, treating, or ameliorating sexual dysfunction in female mammals, including methods of treating delayed vaginal engorgement, diminished vaginal lubrication, pain or discomfort with intercourse (dyspareunia), diminished vaginal sensation, diminished vaginal orgasm, diminished clitoral sensation or diminished clitoral orgasm, or of treating vaginal pain by stimulating peripheral pelvic nerve release of nitric oxide (NO). The treatment methods of the present invention include the improvement in a female of the physiological state associated with sexual activity including appropriate vaginal lubrication, vaginal sensation, vaginal orgasm, or clitoral sensation, but in whom one of the above-mentioned abnormal conditions may not be present.

BACKGROUND OF THE INVENTION

Sexual response in mammals is mediated by a balanced interplay between the sympathetic and parasympathetic nervous systems. Vasocongestion, or erectile tumescence in both the male and female, is largely mediated by parasympathetic (cholinergic) outflow, whereas orgasm is predominantly sympathetic (adrenergic).

Sexuality in human females encompasses multiple components including physiological, psychological, social and emotional factors. However, the first phase of the female sexual response is mediated by a combination of vasocongestive and neuromuscular events which include increased clitoral length and diameter, as well as increased vaginal lubrication, wall engorgement and increased luminal diameter.

The clitoris is the homologue of the penis, arising from the embryological genital tubercle. As a result, the two organs have similar structural and arousal response mechanisms. The clitoris consists of a cylindrical, erectile organ composed of three parts: the outermost glans or head, the middle corpus or body, and the innermost crura. The body of the clitoris consists of paired corpora cavernosa of about 2.5 cm in length and lacks a corpus spongiosum. During sexual arousal, blood flow to the corpora cavernosa of the clitoris cause their enlargement and tumescence. The clitoris plays a major role during sexual activity in that it induces local autonomic and somatic reflexes causing vaginal vasocongestion, engorgement, and subsequent transduction, lubricating the introital canal making the sexual act easier, more comfortable, and more pleasurable.

Vaginal wall engorgement enables a process of plasma transduction to occur, allowing a flow through the epithelium and onto the vaginal surface. Plasma transduction results from the rising pressure in the vaginal capillary bed during the sexual arousal state. In addition, there is an increase in vaginal length and luminal diameter, especially in the distal ⅔ of the vaginal canal.

The vaginal canal is lubricated primarily from a transudate originating from the subepithelial vascular bed passively transported through the interepithelial spaces sometimes referred to as intercellular channels. Additional moistening during intercourse comes from secretion of the paired greater vestibular or Bartholin's glands.

These events depend upon sufficient blood flow to these organs during sexual arousal, and a physiologic disorder which impairs this blood flow, resulting in female vasculogenic sexual dysfunction, can ultimately lead to or exacerbate a pre-existing psychological condition.

The arterial supply to the vagina is derived from an extensive network of branching vessels surrounding it from all sides. The anterior branch of the internal iliac artery continually bifurcates as it descends through the pelvis with a series of the newly generated vessel, each supplying the vagina to some degree. After giving off an obturator artery branch, the umbilical and the middle rectal arteries diverge off to supply a superior and inferior vesical artery, respectively. Between the umbilical and the mid-rectal branches there is generation of a uterine artery which further bifurcates to give the vaginal artery. The internal pudendal and accessory pudendal artery also sends a branch. Finally the common clitoral artery sends a branch to the vaginal muscularis.

The main arterial supply to the clitoris is from the ilio-hypogastric-pudendal arterial bed. The internal pudendal artery is the last anterior branch of the internal iliac artery. Distally, the internal pudendal artery traverses Alcock's canal, a position of the obturator fascia and lies on the inner side in supposition to the ischio-pubic ramis. In this latter location, the artery is susceptible to blunt perineal trauma. The internal pudendal artery terminates as it supples the inferior rectal and perineal artery, which supplies the labia. The common clitoral artery continues to the clitoris. This artery bifurcates into a dorsal clitoral artery and a cavernosal clitoral artery.

Based upon animal research, it has been found that central nervous system areas primarily implicated in sexual arousal include the medial pre-optic, anterior hypothalamic region and related limbic-hippocampal structures of the brain.

Female sexual dysfunction which has its origin in abnormal arterial circulation into the vagina or clitoris during sexual stimulation may be considered a disorder of arousal. This vasculogenic female sexual dysfunction may include such clinical symptoms as delayed vaginal engorgement, diminished vaginal lubrication, pain or discomfort with intercourse (dyspareunia), diminished vaginal sensation, diminished vaginal orgasm, diminished clitoral sensation or diminished clitoral orgasm.

Moreover, traumatic injury to the ilio-hypogastric-pudendal arterial bed from pelvic fractures-or blunt perineal trauma may also result in diminished vaginal/clitoral blood flow following sexual stimulation and fall into the vasculogenic dysfunction category.

Vaginal pain may derive from a general vaginal hyperalgesia or sensitivity to stimulation associated with coitus (dyspareunia) when there has been sufficient genital engorgement and lubrication.

Treatment of female sexual dysfunction is gradually evolving as more clinical and basic science studies are dedicated to the investigation of this medical problem. Female sexual complaints are not all psychological in pathophysiology, especially for those individuals who may have a component of vasculogenic dysfunction contributing to the overall female sexual complaint. Aside from hormone replacement therapy, medical management of female sexual dysfunction remains in the early phases of development. All non-hormonal medications listed below are undergoing safety and efficacy testing for the treatment of male erectile dysfunction and are only in the experimental stage for the treatment of female sexual dysfunction.

Estrogen replacement therapy is presently used in post-menopausal women (either spontaneous or surgical) for the treatment of hot flashes, prevention of osteoporosis, and diminishment of the risk of heart disease. Estrogen replacement results in improved clitoral sensitivity, increased libido and decreased pain/burning during intercourse. Local or topical estrogen application relieves symptoms of vaginal dryness, burning, urinary frequency and urgency. No clinical evidence exists thus far that the use of topical estrogen cream results in relief of sexual complaints other than local vaginal pain or vaginal dryness.

Methyl testosterone may be used in combination with estrogen in post-menopausal women for symptoms of inhibited desire, dyspareunia or lack of vaginal lubrication. Topical vaginal testosterone is used for treatment of vaginal lichen planus. These women, usually elderly, are noted to have clitoral enlargement, increased facial hair and increased sexual appetite. There are conflicting reports regarding the benefit of methyl testosterone for the treatment of inhibited desire and/or vaginismus in pre-menopausal women.

In men, topical application of prostaglandin E1 combined with a skin enhancer such as SEPA is presently demonstrating initial success in pilot Phase II clinical trials. Clinical studies are necessary to determine the safety and efficacy of this medication used as a topically-administered vaginal vasoactive agent in the treatment of vasculogenic female dysfunction. However, one study has demonstrated increased clitoral blood flow and clitoral erection following local prostaglandin E1 injection into clitoral corporal erectile tissues.

Sildenafil functions as a selective type 5 (i.e. c-GMP specific) phosphodiesterase inhibitor, and acts to decrease the metabolism of c-GMP, the second messenger in nitric oxide mediated male erectile response. An oral formulation of this medication has proven to be safe and effective in improving erectile duration and rigidity. In females, nitric oxide/NOS exists in human vaginal and clitoral tissue. Sildenafil may prove useful alone, or possibly in combination with other vasoactive agents for the treatment of vasculogenic female sexual dysfunction. Clinical studies evaluating the efficacy of this medication in women are needed.

Phentolamine is currently available as an oral preparation with rapid absorption and metabolism. Phentolamine's mechanism of action inducing vascular smooth muscle relaxation occurs via alpha-adrenergic blockade as well as by direct smooth muscle relaxation. Studies are currently in progress using this medication in women with female sexual dysfunction.

Despite these advances in the discovery of agents effective to treat female sexual dysfunction, there still exists a need for the discovery of additional compounds useful in the treatment of this condition.

SUMMARY OF THE INVENTION

In one embodiment, the present invention provides a method of treating or ameliorating sexual dysfunction in female mammals by administering to a mammal in need of such treatment a therapeutically effective amount of a compound which acts upon mid-brain pathways to increase blood flow to the ilio-hypogastric-pudendal arterial bed and genitalia.

In another embodiment, the present invention provides a method of combating vaginal pain by administering to a mammal in need of such treatment a therapeutically effective amount of a compound which acts upon mid-brain pathways to stimulate peripheral nerve release of nitric oxide (NO) in the pelvic nerve network, preferably from non-adrenergic, non-cholinergic (NANC) nerves. The vaginal pain may be general hyperalgesia (non-specific increased vaginal sensitivity) or pain associated with intercourse (dyspareunia).

The selected compound is one which acts upon any of the mid-brain pathways which include the dopaminergic, serotonergic, oxytocinergic or nitroxidergic mid-brain pathways.

In another embodiment, the present invention provides a method for producing an effective vasocongestive arousal in a female comprising administering a therapeutically effective amount of a compound which acts upon a mid-brain dopaminergic, serotonergic, oxytocinergic or nitroxidergic pathway to increase blood flow to the ilio-hypogastric-pudendal arterial bed and genitalia. By effective vasocongestive arousal is meant clitoral erection, vaginal and labialar engorgement, and lubrication adequate for intercourse.

In yet another embodiment, the present invention provides a means of treating vaginal engorgement insufficiency in a female mammal comprising administering a therapeutically effective amount of a compound which acts upon a mid-brain dopaminergic, serotonergic, oxytocinergic or nitroxidergic pathway to increase blood flow to the ilio-hypogastric-pudendal arterial bed and genitalia.

In another embodiment, the present invention provides a method of treating clitoral erectile insufficiency in a female mammal comprising administering a therapeutically effective amount of a compound which acts upon a mid-brain dopaminergic, serotonergic, oxytocinergic or nitroxidergic pathway to increase blood flow to the ilio-hypogastric-pudendal arterial bed and genitalia.

In still another embodiment, the present invention comprises a method of treating dyspareunia in a female mammal comprising administering a therapeutically effective amount of a compound which acts upon a mid-brain dopaminergic, serotonergic, oxytocinergic or nitroxidergic pathway to facilitate peripheral nerve release of NO in the pelvic nerve network, preferably from non-adrenergic, non-cholinergic nerves.

In the embodiments described above, an androgen may optionally be co-administered with the primary active compound, wherein co-administration of the androgen enhances or potentiates the effect of the principal therapeutic agent.

In yet another embodiment, the present invention provides a means of diagnosing the presence or absence of sexual dysfunction in a female mammal. The diagnostic method comprises the steps of administering apomorphine alone or in combination with an androgen and observing any change in physiologic response associated with sexual activity. A change indicates the presence of sexual dysfunction.

DETAILED DESCRIPTION

Figure 1:
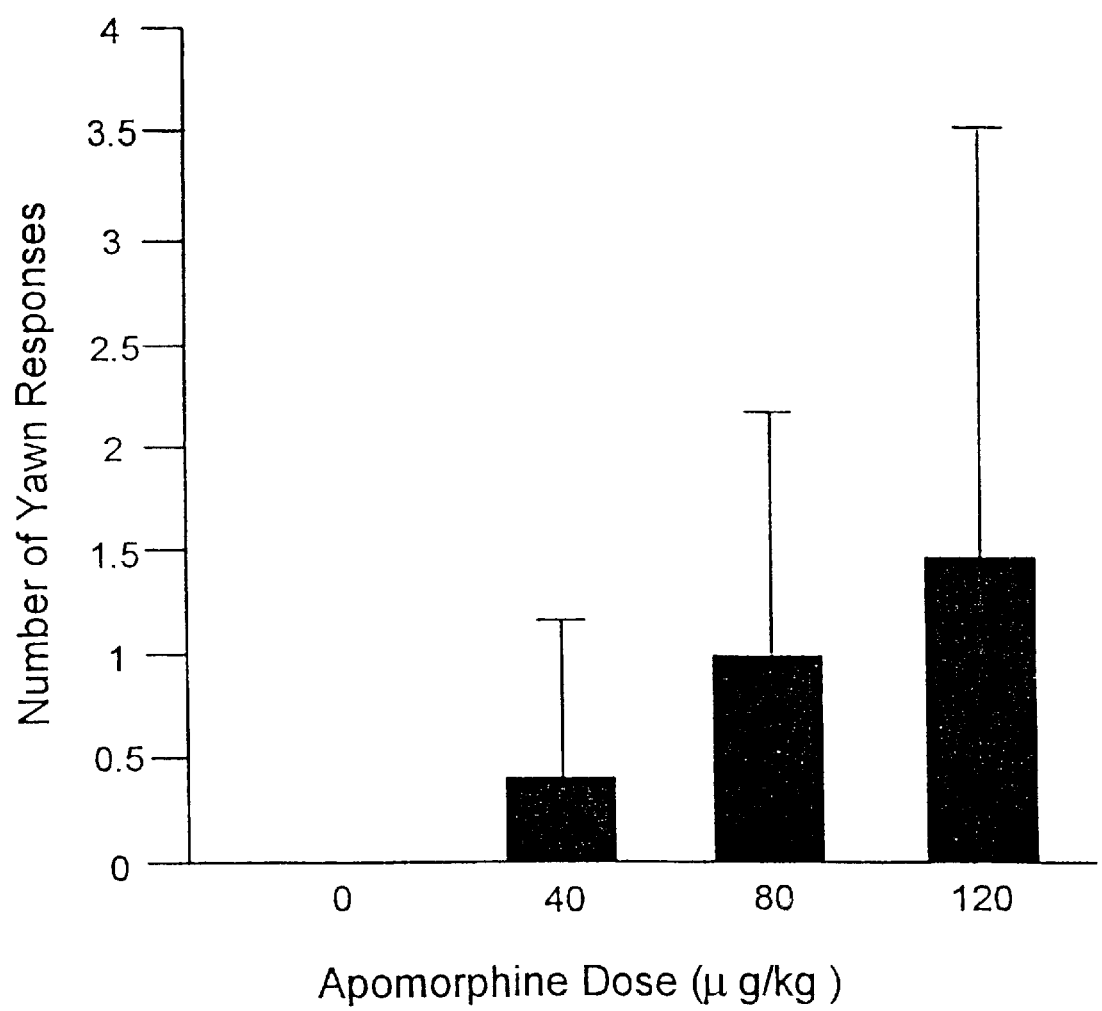
FIG. 1 is a histogram depicting yawning response of female test animals following administration, in a first study, of various doses of apomorphine.

As used throughout this specification and the appended claims, the following terms have the meanings ascribed to them.

By "androgen" is meant any compound recognized in the art to elicit an androgenic effect, either in their free base form or in the form of a salt or pro-drug by acting on androgen receptors in an agonist-like manner. Also included in the definition of "androgen" is any compound which mimics an art-recognized androgen, which compound stimulates or activates androgenic pathways. Representative androgens include testosterone, dihydrotestosterone (DHT), dehydro-epiandrostenedione (DHEA), and dehydroepiandrostenedione sulfate (DHEAS).

The terms "acute dose" or "acute administrations" of a drug mean the scheduled administration of a drug to a patient on an as-needed basis at a dosage level determined by the attending physician to elicit a relatively immediate desired reaction in the patient, given the patient's age and general state of health.

A "sub-acute dose" is a dose of the drug at a lower level than that determined by the attending physician to be required for an acute dose, as described above. Sub-acute doses may be administered to the patient on an as-needed basis, or in a chronic, or on-going dosing regimen.

The terms "continuous dose" or "chronic administration" of a drug mean the scheduled administration of a drug to the patient on an on-going day-to-day basis.

The term "co-administration" of two or more drugs denotes the simultaneous acute dosing of the drugs, or the sequential administration of two or more drugs with a period of delay between their administration. One drug may be administered in a chronic dose, with the other drug(s) administered on an acute or as-needed basis.

By the term "treatment of sexual dysfunction" is meant the treatment, prevention, or amelioration of the conditions of delayed vaginal engorgement, diminished vaginal lubrication, pain or discomfort with intercourse (dyspareunia), diminished vaginal sensation, diminished vaginal orgasm, diminished clitoral sensation, diminished clitoral orgasm, or generalized vaginal pain. In addition, the term "treating sexual dysfunction," as contemplated in this application, means the improvement in a female of the physiological state associated with sexual-activity which includes appropriate vaginal lubrication, vaginal sensation, vaginal orgasm, or clitoral sensation, but in whom one of the above-mentioned abnormal conditions may not be present.

It is to be understood that the determination of the appropriate dose regimen for a given patient is well within the skill of the attending physician. Since the proper dose varies from person to person based on the age and general state of health, it is a common practice of physicians to "dose-titrate" the patient; that is, to start the patient on a dosing regimen which is at a level below that required to produce the desired response, and gradually increase the dose until the desired effect is achieved.

The term "effective vasocongestive arousal" means, in the female, tumescent clitoral erection, engorgement, swelling and lubrication of the vagina and engorgement and swelling of the labia. Such arousal conditions may result from a net increase in blood flow to genital tissues caused by (a) increased inflow with normal outflow, (b) increased inflow with decreased (vasoconstricted) outflow, or (c) normal inflow with decreased outflow.

Compounds useful in the methods of the present invention are those compounds which are known to act upon the mesencephalon or mid-brain nerve pathways to increase blood flow to the ilio-hypogastric-pudendal arterial bed and genitalia or to act on a mid-brain neural pathway to stimulate vasodilation, and genital engorgement and lubrication. This action may be by, for example, peripheral release of nitric oxide (NO) from non-adrenergic, non-cholinergic (NANC) nerve cells in the pelvic region. Examples of these compounds include those which are known to act on any of the dopaminergic, serotonergic, oxytocinergic or nitroxidergic mammalian mid-brain pathways to produce such peripheral effects.

Dopaminergic pathway compounds include apomorphine, bromocriptine, lisuride, methergoline, pergolide, piribidil, and quinpirole.

Serotonergic pathway compounds include serotonin receptor agonists such as 1-(2,5-dimethoxy-4-iodophenyl)-laminopropane, 5-methoxytryptamine, a-methyl-5hydroxytryptamine, 2-methyl-5-hydroxytryptamine, N-acetyl-5hydroxytryptamine buspirone, and sumatriptin. Oxytocinergic pathway compounds include oxytocin analogues such as isotocin, carbetocin, Lys-conopressin, deaminooxytocin, mesotocin, antocin, glumitocin, aspargitocin, valitocin, asvatocin, phasvatocin, and seritocin.

The preferred compound for use in the methods of the present invention is apomorphine or one of its salts, esters or pro-drug forms. Apomorphine, (R)-5,6,6a, 7-tetrahydro-6-methyl-(4H)-dibenzo[de,g]quinoline-10,11-diol, is a derivative of morphine obtained by treatment of the latter with concentrated hydrochloric acid (L. Small, et al., *J. Org. Chem.*, 5:334 (1940)) or by heating morphine with zinc chloride (Mayer, Ber., 4:171 (1871)). The compound has the chemical structure shown below and possesses a chiral center at position 6a. The total synthesis of the racemic mixture is reported by J. L. Neumeyer, et al., *J. Pharm. Sci.*, 59:1850 (1970) and the synthesis of the separate enantiomers by V. J. Ram and J. Neumeyer, *J. Org. Chem.*, 46:2830 (1981).

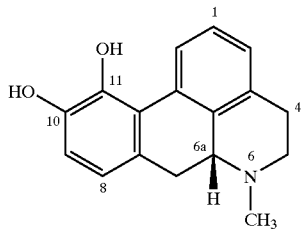

The compound possesses a basic nitrogen atom at position 6 and is thus capable of existing in the free base form as well as acid addition salt forms. The compound may be administered as the free base or in the form of one of its pharmaceutically acceptable salts or pro-drug derivatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66:1–19 (1977). The salts are prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

The term "pro-drug" refers to compounds that are rapidly transformed in vivo to yield the parent compound, as for example, by hydrolysis in blood. T. Higuchi and V. Stella provide a thorough discussion of the pro-drug concept in "Pro-drugs as Novel Delivery Systems", Vol. 14 of the A.C.S. Symposium Series, American Chemical Society (1975).

Examples of esters useful as pro-drugs for compounds containing carboxyl groups may be found on pages 14–21 of "Bioreversible Carriers in Drug Design: Theory and Application," edited by E. B. Roche, Pergamon Press (1987).

The term "pro-drug ester group" refers to any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Apomorphine has been shown to be effective in facilitating and maintaining erectile response in males. Formulations containing apomorphine for this purpose, and methods of treating erectile dysfunction in males is disclosed in U.S. Pat. No. 5,770,606, the entire contents of which are incorporated herein by reference.

The studies which are presented below illustrate that apomorphine also enhances the sexual response in females, with its effect being potentiated by co-administration of an androgen. The preferred androgen is testosterone or one of its pharmaceutically acceptable salts, esters or pro-drugs.

For an optimal vasocongestive arousal response in the female, steady state circulating serum and mid-brain tissue levels of apomorphine should be maintained within a relatively closely defined range. The drug is preferably administered in a formulation which delivers the drug to the system while maintaining and not exceeding the desired systemic levels of the drug. Methods known to the practitioner of the pharmaceutical formulation arts which accomplish this may be used. For example, the drug may be delivered to the system by means of a solid oral formulation, by a liquid formulation, including one applied sub-lingually; by a tablet, lozenge, or lollipop held in the mouth and absorbed buccally; by means of a suppository formulation administered intravaginally or rectally; by a powder, gel, or suspension, or an intra-nasal spray formulation. Formulations for the intra-nasal administration of apomorphine are taught, for example, in U.S. Pat. No. 5,756,483 to Merkus; buccal or sub-lingual formulations for the administration of apomorphine are taught in U.S. Pat. No. 5,888,534 to El-Rashidy et al. The teachings of both patents are incorporated herewith by reference.

The drug may also be administered in a sterile parenteral formulation by sub-cutaneous or intramuscular route, although sub-lingual, buccal, intra-nasal, and suppository formulations are preferred because of their greater ease of administration and the resulting greater potential for patient acceptance.

Sublingual dosage forms, usually containing about 1 to about 12 milligrams, preferably about 2.5 to about 10 milligrams of apomorphine, are useful in treating the symptoms of female vasculogenic sexual dysfunction, including its symptomatic manifestations without nausea or other undesirable side effects. Plasma concentrations of apomorphine are preferably at between about 0.1 to 6 nanograms per milliliter, preferably between about 0.3 to about 4 nanograms per milliliter, and more preferably between about 1 to about 2 nanograms per milliliter, sufficient to induce clitoral erection, vaginal and labialar engorgement and lubrication adequate for intercourse (i.e. "effective vasocongestive arousal") but less than the amount that induces nausea.

The apomorphine is administered in the time period immediately prior to sexual activity, generally during the period between about 2 minutes and 120 minutes prior to sexual activity, preferably during the period between about 2 minutes and about 60 minutes prior to sexual activity, so as to achieve desired serum and mid-brain tissue levels of the drug.

Apomorphine has been recognized for use as an emetic when administered subcutaneously in about a 5-milligram dose. For the purposes of the present invention, apomorphine or a similarly acting dopamine receptor agonist is administered in an amount sufficient to excite cells in the mid-brain region of the patient but with minimal side effects. This cell excitation is believed to be part of a cascade of stimulation that is likely to include neurotransmission with serotonin and oxytocin.

The dopamine receptors in the mid-brain region of a patient can be stimulated to a degree sufficient to cause an erectile response by the administration, preferably sublingually, of apomorphine so as to maintain a plasma concentration of apomorphine of no more than about 5.5 nanograms per milliliter (5.5 ng/ml). The sublingual administration usually takes place over a time period in the range of about 1 to about 10 minutes, or longer. The amount of apomorphine administered sublingually over this time period is preferably in the range of about 10 micrograms per kilogram ($\mu$g/kg) of body weight to about 100 $\mu$g/kg of body weight, more preferably from about 25 $\mu$g/kg to about 80 $\mu$g/kg of body weight.

Co-administration of an androgen potentiates the effect of apomorphine in eliciting sexual arousal, as shown in the studies described below. Representative suitable androgens for co-administration with apomorphine in the methods of the present invention include testosterone, dihydrotestosterone (DHT), dehydroepiandrostenedione (DHEA), and pharmaceutically acceptable salts, esters and pro-drugs of the foregoing, including testosterone undecanoate and dehydroepiandrostenedione sulfate(DHEAS).

The androgen is co-administered with the apomorphine, in one alternative dosing regimen, simultaneously, with both drugs being administered in acute doses, or with the apomorphine being administered in an acute dose, with the androgen administered in a sub-acute dose. Alternatively, the androgen may be administered at a chronic low dose, with the apomorphine administered in an as-needed dose, or with the apomorphine administered chronically, with the androgen administered on an as-needed basis.

Sustained release formulations for administration of a chronic low-dose of the androgen may take the form of well-known depot formulations, esters or pro-drugs which undergo bioconversion to release the androgen, or transdermal patch formulations.

In the studies shown below, the potentiating influence of an androgen on the sexual arousal effects of apomorphine in female rats were found to be maximal when the androgen was administered about thirty-six hours prior to the administration of apomorphine. However, this delayed effect may have been due to pharmacokinetic effects associated with the mode of delivery or the form of the drug employed. However, these data suggest that slower-acting forms of androgen should be administered in the interval between about 2 to about 48 hours prior to the administration of apomorphine. The androgen may be made more readily available by administration in a form which delivers the drug to the blood stream more rapidly. This can be achieved by direct application of the androgen to mucosal tissue, such as by rectal, vaginal, intranasal, buccal, or sub-lingual administration. When a faster-acting form of androgen is employed, the the androgen may be administered in the period 2-hours prior to administration of the apomorphine, or concomitantly therewith.

In one alternative dosing regimen for co-administering an androgen and apomorphine to humans, the androgen is administered in an oral dosage form prior to the apomorphine, as in a pill, tablet, lozenge, or capsule form. In a second alternative dosing regimen, the androgen is administered in a rapidly-available form concomitantly with the apomorphine.

Andriol, (Organon, 375 Mt. Pleasant Ave., West Orange, N.J. 07052) is a rapidly available oral dosage form of testosterone undecanoate packaged as an oil solution sealed in capsules. This formulation rapidly delivers testosterone by bypassing the liver and making the testosterone available through the lymphatic system.

The present invention thus contemplates, in one embodiment, a combination package having unit dosage forms of both apomorphine and an androgen, preferably testosterone. Both dosage forms may be in the form of rapidly acting doses of the two drugs, such as testosterone undecanoate described above, and a buccal, sub-lingual, or intra-nasal dosage form of apomorphine.

Illustrative preferred sublingual dosage forms of apomorphine are set forth in Table I, below.

TABLE I

150-Milligram Apomorphine Hydrochloride Sublingual Tablets

| 3-mg Tablet | |
| --- | --- |
| Apomorphine Hydrochloride | 2.00 wt % |
| Mannitol | 66.67 wt % |
| Ascorbic Acid | 3.33 wt % |
| Citric Acid | 2.00 wt % |
| Avicel PH 102 | 15.00 Wt % |
| Methocel E4 | 10.00 Wt % |
| Aspartame | 0.67 wt % |
| Magnesium stearate | 0.33 wt % |
| 4-mg Tablet | |
| Apomorphine Hydrochloride | 2.66 wt % |
| Mannitol | 66.00 wt % |
| Ascorbic Acid | 3.33 wt % |
| Citric Acid | 2.00 wt % |
| Avicel PH102 | 15.00 wt % |
| Methocel E4M | 10.00 Wt % |
| Aspartame | 0.67 wt % |
| Magnesium stearate | 0.33 wt % |
| 5-mg Tablet | |
| Apomorphine Hydrochloride | 3.33 wt % |
| Mannitol | 65.34 wt % |
| Ascorbic Acid | 3.33 wt % |
| Citric Acid | 2.00 wt % |
| Avicel PH102 | 15.00 wt % |
| Methocel E4M | 10.00 wt % |
| Aspartame | 0.67 wt % |
| Magnesium stearate | 0.33 wt % |

If desired, and in order to facilitate absorption and thus bioavailability, the presently contemplated dosage forms can also contain, in addition to tableting excipients, β-cyclodextrin or a β-cyclodextrin derivative such as hydroxypropyl-β-cyclodextrin (HPBCD). Illustrative dosage forms containing HPBCD are shown in Tables II and III, below.

TABLE II

Apomorphine Hydrochloride Sublingual Tablets With Hydroxypropyl-β-Cyclodextrin

|  | mg/Tab |
|---|---|
| Apomorphine hydrochloride | 4.0 |
| HPBCD | 5.0 |
| Ascorbic acid | 10.0 |
| PEG 8000 | 39.5 |
| Mannitol | 39.5 |
| Aspartame | 2.0 |
| Total | 100.0 |

TABLE III

Apomorphine Hydrochloride Sublingual Tablets With β-Cyclodextrin

|  | mg/Tab |
|---|---|
| Apomorphine hydrochloride | 5.0 |
| β-Cyclodextrin | 20.0 |
| Ascorbic acid | 5.0 |
| Mannitol | 68.9 |
| Magnesium stearate | 1.0 |
| D&C Yellow 10 aluminum lake | 0.1 |
| TOTAL | 100.0 |

The onset of nausea can be obviated or delayed by delivering apomorphine at a controlled dissolution rate so as to provide circulating serum levels and midbrain tissue levels of apomorphine sufficient for an effective vasocongestive arousal without inducing nausea. When apomorphine is administered at or near the relatively higher amounts of the aforementioned dosage range, the likelihood of nausea onset can be reduced by concurrent administration of a ganglionic agent (inhibitor of ganglionic response) such as nicotine or lobeline sulfate. For this purpose, the weight ratio of apomorphine to ganglionic agent is in the range of about 10 to about 1.

Other antiemetic agents that can be used in conjunction with apomorphine are antidopaminergic agents such as metoclopramide, and the phenothiazines, e.g., chlorpromazine, prochlorperazine, pipamazine, thiethylperazine, oxypendyl hydrochloride, and the like. Also suitable are the serotonin (5-hydroxytryptamine or 5-HT) antagonists such as domperidone, ondansetron (commercially available as the hydrochloride salt under the designation Zofran©), and the like, the histamine antagonists such as buclizine hydrochloride, cyclizine hydrochloride, dimenhydrinate (Dramamine), and the like, the parasympathetic depressants such as scopolamine, and the like, as well as other anti-emetics such as metopimazine, trimethobenzamide, benzauinamine hydrochloride, diphenidol hydrochloride, and the like.

Nicotine-containing dosage forms and domperidone-containing dosage forms are illustrated in Table IV, below.

TABLE IV

Apomorphine Hydrochloride Sublingual Tablets Containing an Anti-Emetic Agent

|  | mg/Tab |
|---|---|
| Apomorphine Hydrochloride | 5.0 |
| Ascorbic Acid | 5.0 |
| Mannitol | 67.9 |
| Magnesium Stearate | 1.0 |
| Nicotine | 1.0 |
| β-Cyclodextrin | 20.0 |
| D&C Yellow aluminum lake | 0.1 |
| TOTAL | 100.0 |
| Apomorphine Hydrochloride | 5.0 |
| Ascorbic Acid | 5.0 |
| Mannitol | 58.9 |
| Magnesium Stearate | 1.0 |
| Domperidone | 10.0 |
| β-Cyclodextrin | 20.0 |
| D&C Yellow 10 aluminum lake | 0.1 |
| TOTAL | 100.0 |

The preferred sublingual dosage forms dissolve within a time period of at least about 2 minutes but less than about 10 minutes. The dissolution time can be longer, however, if desired as long as the desired plasma concentration of apomorphine can be achieved. More preferably, the dissolution time in water for the presently contemplated dosage forms is about 3 minutes to about 5 minutes.

The present invention is illustrated further by the following studies. In the studies described below, the sexual behavior responses that were quantified were yawns and genital licks (the analogous female rat response to penile erections in the male rat). An event was counted as a genital lick when the animal stood on its hind legs, and rapidly and decisively descended (with a concavity of the back) into the genital area and proceeded to lick it. The yawn response is a direct indication of central activation of dopaminergic receptors by a drug (e.g. apomorphine). This pathway is at least in part convergent with the pathway which generates sexual responses. The yawns thereby represent a surrogate marker of sexual response. An event was counted as a yawn when the animal exhibited an involuntary opening of the mouth with the appropriate respiratory movement.

Female Wistar rats (Charles River Laboratories, (251 Ballardvale Street, Wilmington, Mass. 01887-1000, USA) utilized in the studies were housed, prior to each experiment, in plastic shoe-box cages in a climate-controlled room with a 12-hour light/12-hour dark cycle. The rats were allowed free access to food and water except during times of testing. During each test, the rats were placed in hanging cages fitted with Plexiglas® bottoms, in a dark, quiet room where they were allowed to acclimate for 10 minutes. After this period either drug or physiological saline (control) was injected subcutaneously to the back of the neck and subsequent genital licking and yawning responses were observed for 30 minutes from a separate room via a video monitoring system. The standard deviations for both types of responses was determined, and statistical significance was determined using the Student's t-test with $p<0.05$.

All experimental procedures were carried out in accordance with the guidelines established by the Canadian Council of Animal Care. Prior to any testing, each animal was handled by the investigator intermittently for 5 days to allow for acclimation by the animals to handling.

A stock solution of apomorphine hydrochloride, containing the drug at a concentration of 120 micrograms/mL, with 100 micrograms/mL of ascorbic acid in physiological saline, was prepared. The flask containing the mixture was is covered with foil paper to prevent any light-induced decomposition and stored in refrigerator until used.

Testosterone propionate (Aldrich Chemical Co., Milwaukee, Wis., USA) was diluted from a stock solution of 100 mg/ml and dissolved in peanut oil prior to sub-cutaneous administration to animal.

In a first pilot study, randomized blind testing was performed with apomorphine doses of 40 micrograms/kg, 80 micrograms/kg, and 120 micrograms/kg, using saline for control. Doses were obtained by administering different amounts of the stock solution of 120 micrograms/mL. The results are presented in FIGS. 1 and 2 where FIG. 1 shows a dose-dependent yawning response in the test animals.

Figure 2:
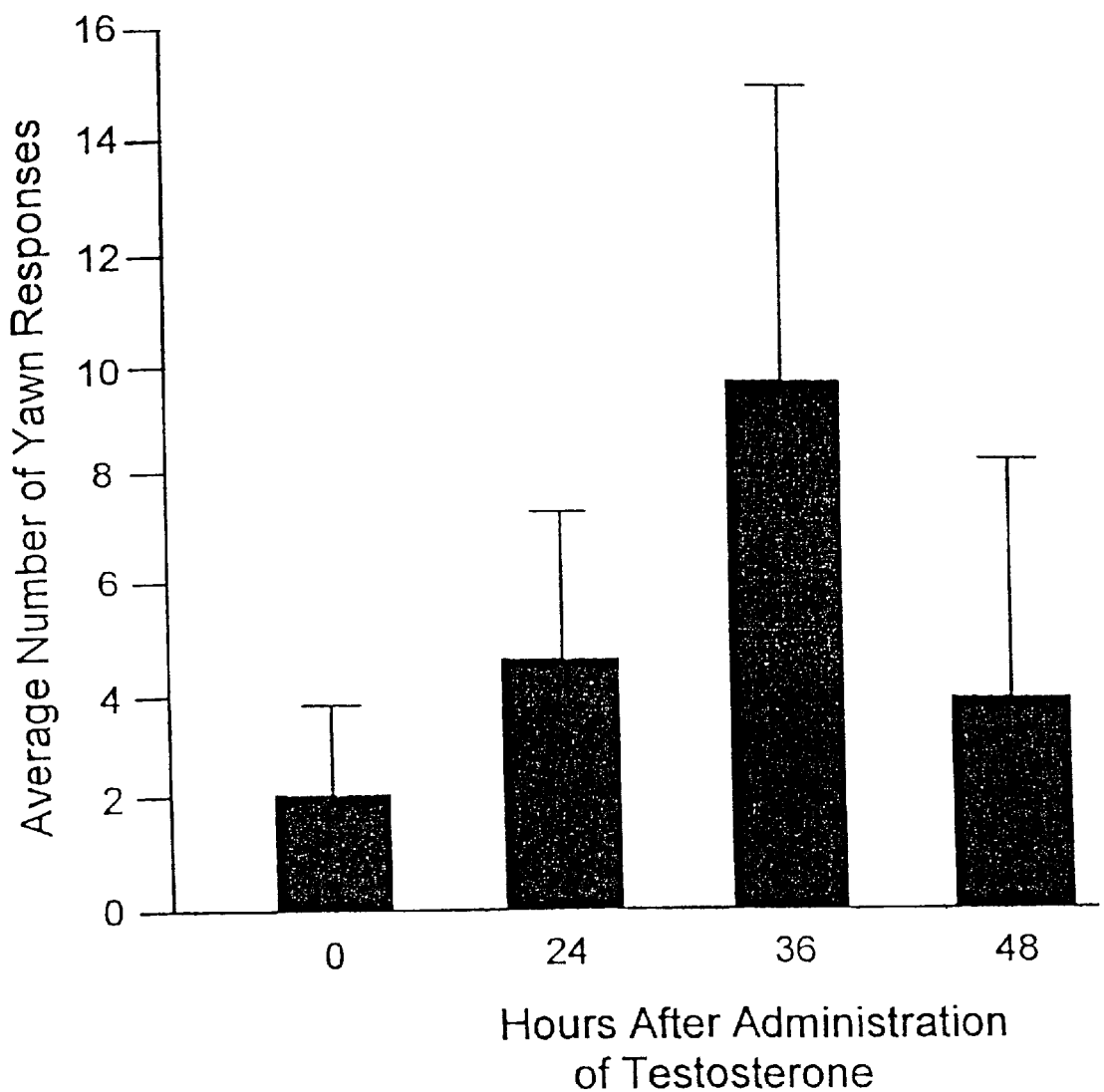
FIG. 2 is a histogram depicting yawning response of female test animals administered, in a-second study, equal 80 microgram/kg doses of apomorphine at various times following the pre-administration of equal 480 microgram/kg doses of testosterone.

In a second study, the potentiating influence of an androgen, testosterone, on the effects of apomorphine on sexual response in female rats was observed. Testosterone was administered at a dosage of 480 micrograms/kg, with 80 microgram/kg doses of apomorphine being subsequently administered at times 0, 24, 36 and 48 hours following administration of the testosterone. The results are shown in FIG. 2 where it was observed that the maximum number of apomorphine-induced yawing responses were observed when apomorphine was administered 36 hours following testosterone administration.

Figure 3:
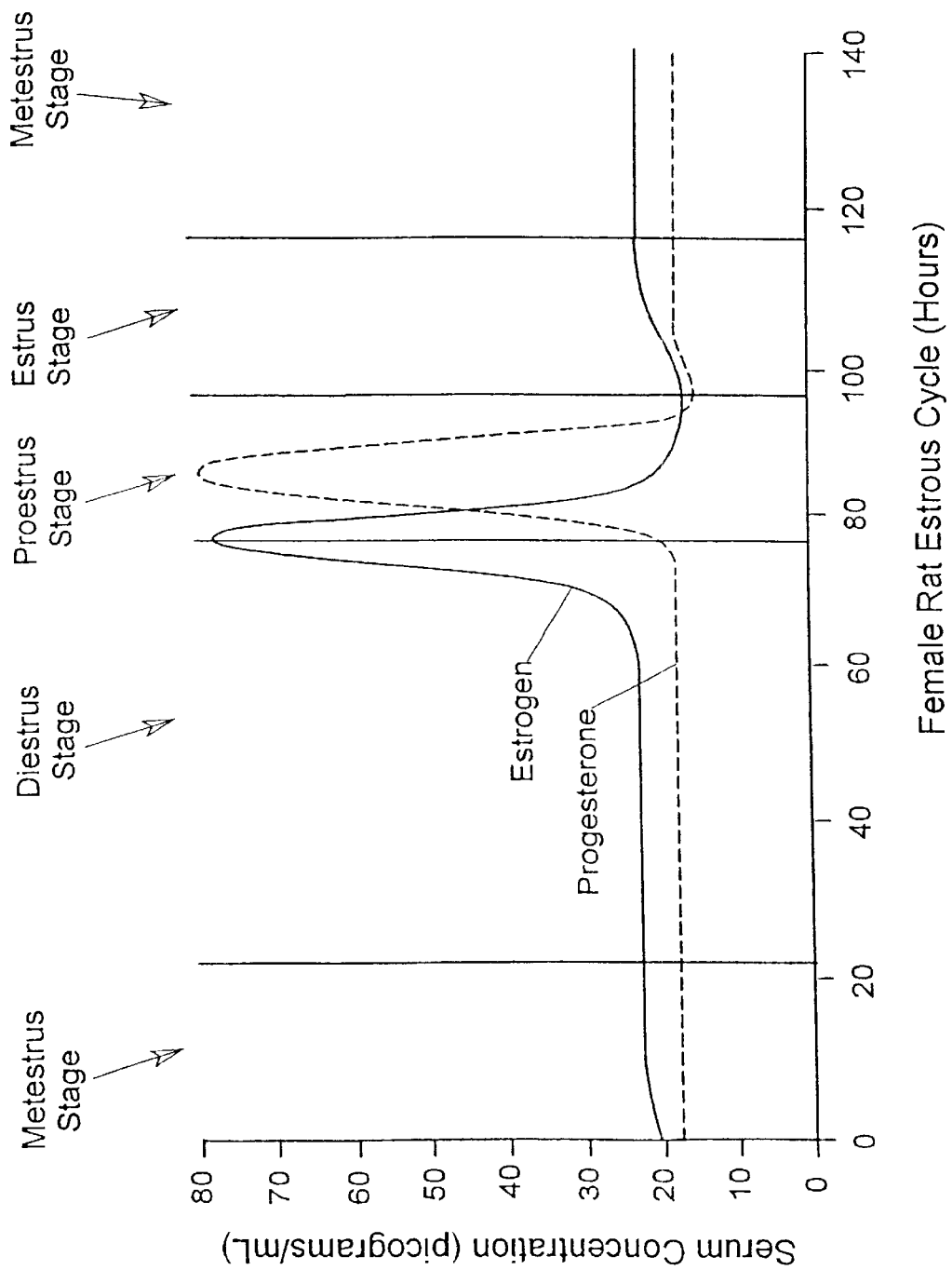
FIG. 3 is a graph showing blood levels of estrogen and progesterone in the female rat during various stages of the rat estrous cycle.

A third study was conducted to determine the effect of administering apomorphine during the various stages of the female rat's estrous cycle. As shown in FIG. 3, the female rat's cycle is divided into 4 stages totaling approximately 4 days: proestrus, estrus, metestrus and diestrus. Estrogen levels are high prior to and at the beginning of proestrus, while progesterone levels are high at the end of proestrus. Both of these hormones are at low levels in metestrus and most of diestrus. Estrogen and progesterone are suggested to exert their fullest influence not until at least 24 hours after secretion. As a consequence, estrogen exerts its fullest influence during the proestrus and estrus stages while progesterone exerts its maximum influence during the metestrus and early diestrus stages.

Figure 4:
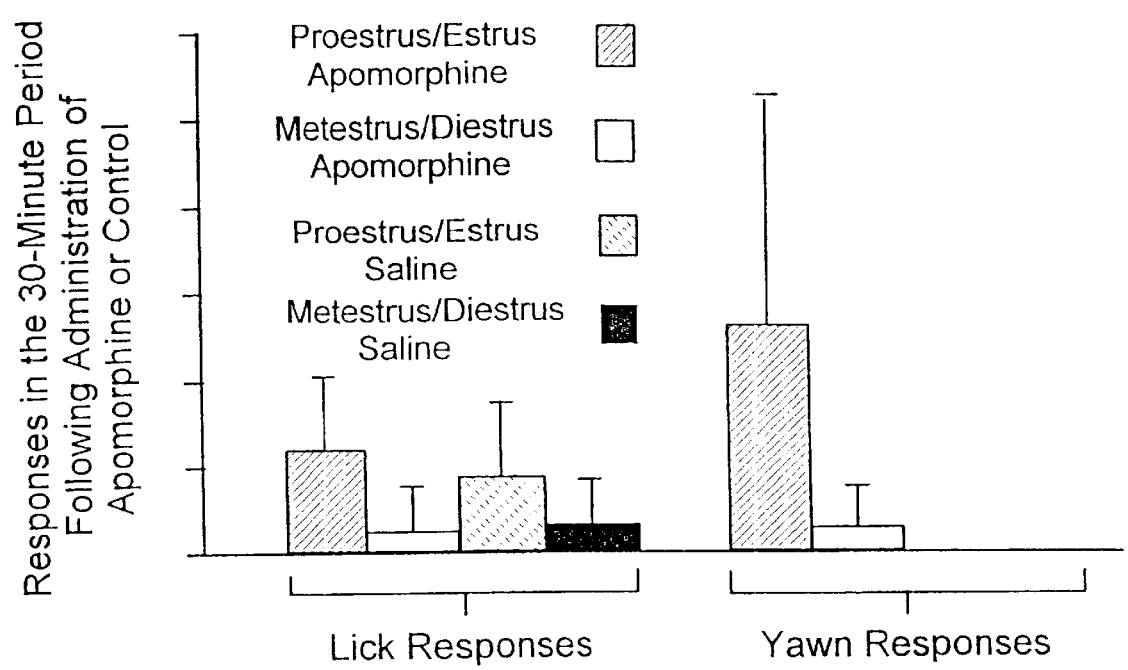
FIG. 4 is a histogram depicting genital licking and yawn response data from a third study in which female rats were administered either saline or 80 micrograms/kg of apomorphine during either the proestrus/estrus or metestrus/diestrus stages of the estrous cycle.

In this study, physiological saline solution or 80 microgram/kg doses of apomorphine were sub-cutaneously administered to intact Wistar rats during either the proestrus/estrus stages or the metestrus/diestrus stages of their cycle. The stages for each animal were determined by examining the epithelial cell type in vaginal smears after the method of Baker, et al., "The Laboratory Rat", Vols. 1–2, Academic Press, 1979. The observed licking and yawn response data are depicted in the histograms appearing in FIG. 4. Apomorphine elicited a significant increase ($p<0.05$) in yawns in the estrogen-influenced proestrus/estrus stages when compared with saline (control). However, no statistically significant effect was seen over control in inducing yawns in the progesterone influenced metestrus/diestrus stages. Apomorphine caused an increase, albeit not statistically significant, in genital licking responses in the proestrus/estrus stages, but no observed difference over control in the metestrus/diestrus stages.

In a fourth study, physiological saline solution (control) or 80 microgram/kg doses of apomorphine were administered to intact female Wistar rats during either the estrogen-influenced proestrus/estrus stages or the progesterone-influenced metestrus/diestrus stages, following prior administration of a 480 microgram/kg dose of testosterone. The results of the second study had shown that the potentiating influence of testosterone on the effects of apomorphine were maximal at around 36 hours after testosterone administration. Thus, in this study, administration of apomorphine to a test animal was timed to fall into the proestrus/estrus stages or the metestrus/diestrus stages of the animal's cycle at the appropriate time following administration of testosterone.

Figure 5:
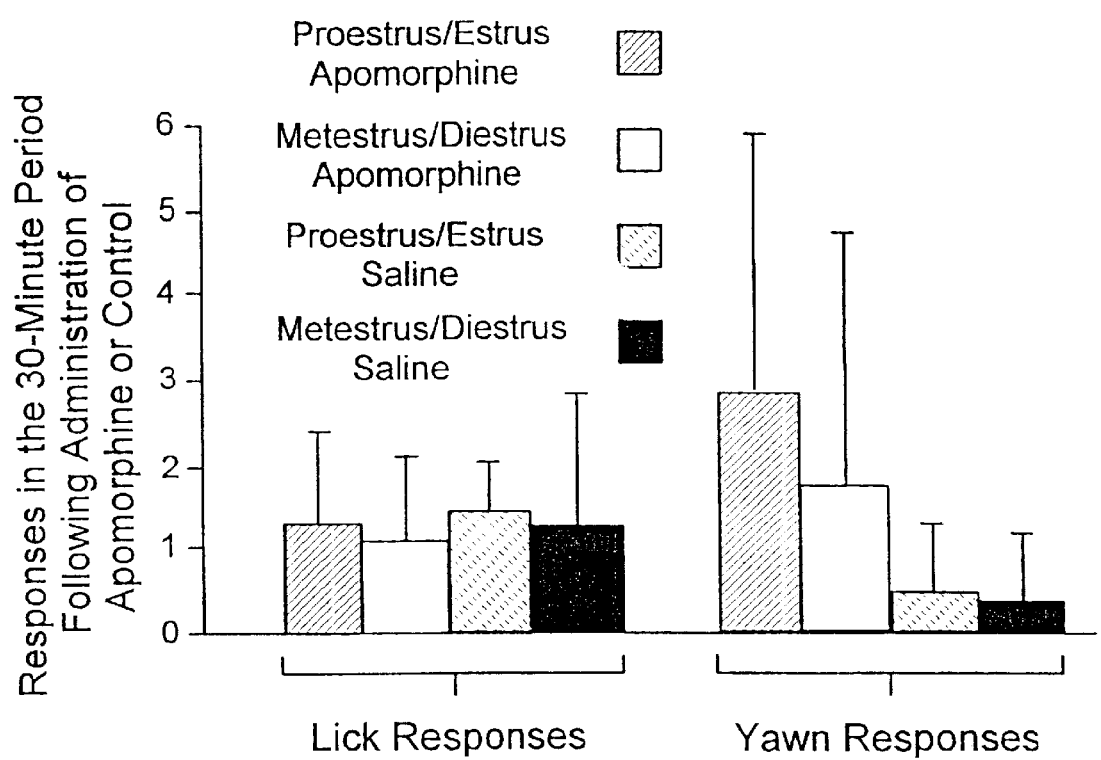
FIG. 5 presents histograms depicting genital licking and yawn response data from a fourth study in which female rats were pre-administered 480 microgram/kg doses of testosterone 36 hours prior to the administration of saline or apomorphine during a particular stage of the estrous cycle. The data compare responses in the proestrus/estrus and the metestrus/diestrus stages following administration of testosterone and either saline or apomorphine.

The genital lick and yawn response data for this study are depicted graphically in FIG. 5. The data show that testosterone pre-treatment normalized the licking response in the female rat regardless of the hormonal state of the animal, or whether it was apomorphine or saline that was administered. However, testosterone pre-treatment increased the yawn responses in those animals to which apomorphine was administered, compared with those that received saline (control).

Figure 6:
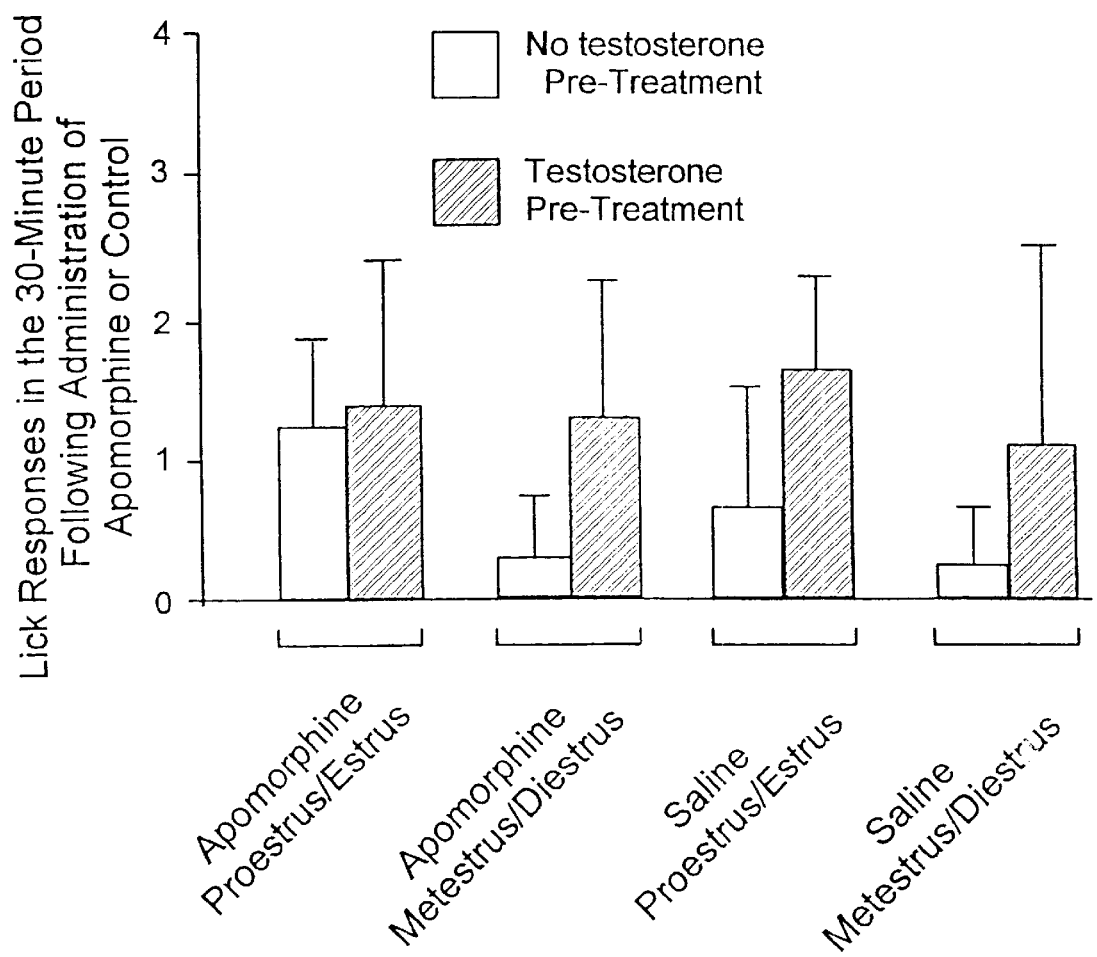
FIGS. 6 and 7 are histograms showing genital lick and yawn response data, respectively, from a study in which female rats were administered either saline or apomorphine, with or without the prior administration of testosterone. Data are presented for both the proestrus/estrus and metestrus/diestrus stages of the estrous cycle.

FIG. 6 depicts genital lick data comparing the administration of doses of 80 microgram/kg doses of apomorphine or physiological saline solution to two groups of intact Wistar rats to which testosterone was either pre-administered (striped bars) or not (open bars). The corresponding data for yawn responses appears in FIG. 7.

Referring to FIG. 6, it can be seen that testosterone pre-treatment increased the observed number of genital licks in apomorphine-treated animals and saline-treated animals in the metestrus/diestrus stages when compared to (a) animals treated with apomorphine and saline in the proestrus/estrus stages or (b) animals given no testosterone pre-treatment and apomorphine during the proestrus/estrus stages.

Figure 7:
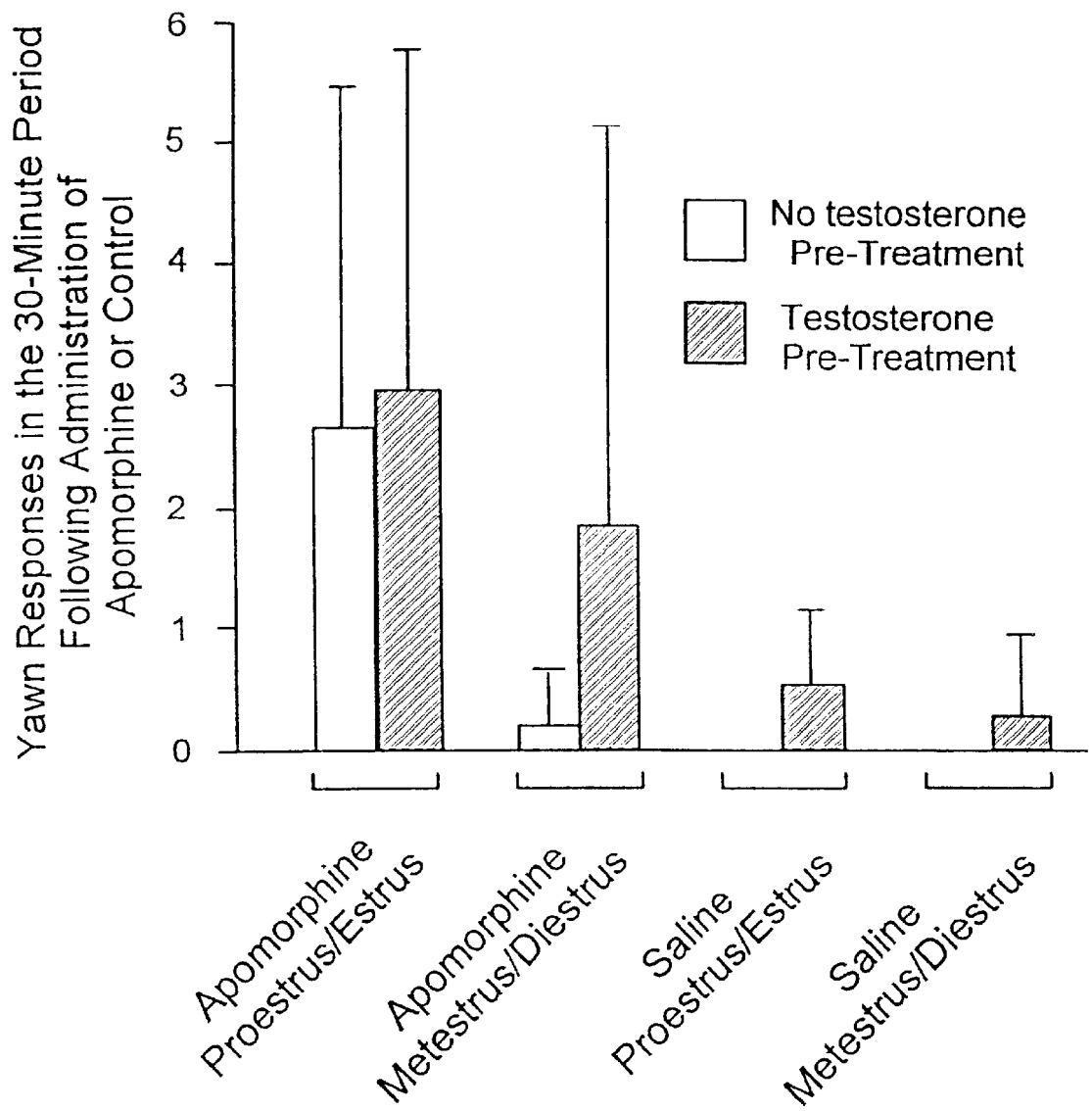

Referring to FIG. 7, pre-treatment of test animals with testosterone also showed a larger increase over control in the number of observed yawn responses in apomorphine-treated animals during the metestrus/diestrus stages when compared to the increase over control in testosterone pre-treated animals given apomorphine during the proestrus/estrus stages.

To study the effect of testosterone pre-treatment in animals which had considerably diminished levels of endogenous hormones, a fifth study was conducted in which the prior experiments were repeated with ovariectomized female Wistar rats. Rats were ovariectomized one month prior to the experiments to ensure there was a minimal level of endogenous hormones (estrogen and progesterone) present in the body. Ovariectomization involved the removal of the ovaries by severing the junction between the fallopian tube and uterine horn after the method detailed by Waynforth, H. and Flecknell, P., "Experimental and Surgical Technique in the Rat," St. Edmundsbury Press, Ltd., 1992. Rats that underwent this procedure were given ketamine and xylazine pre-operatively as anesthetics and 2 doses of 0.1 mL of the antibiotic Tribrissen 24% (Schering Canada, Inc.) and Buprenex for post-operative analgesia respectively. The animals were pre-administered a sub-cutaneous 480 microgram/kg dose of testosterone 36 hours prior to the administration of physiological saline solution or an 80 microgram/kg dose of apomorphine at the appropriate stage of the estrous cycle.

Figure 8:
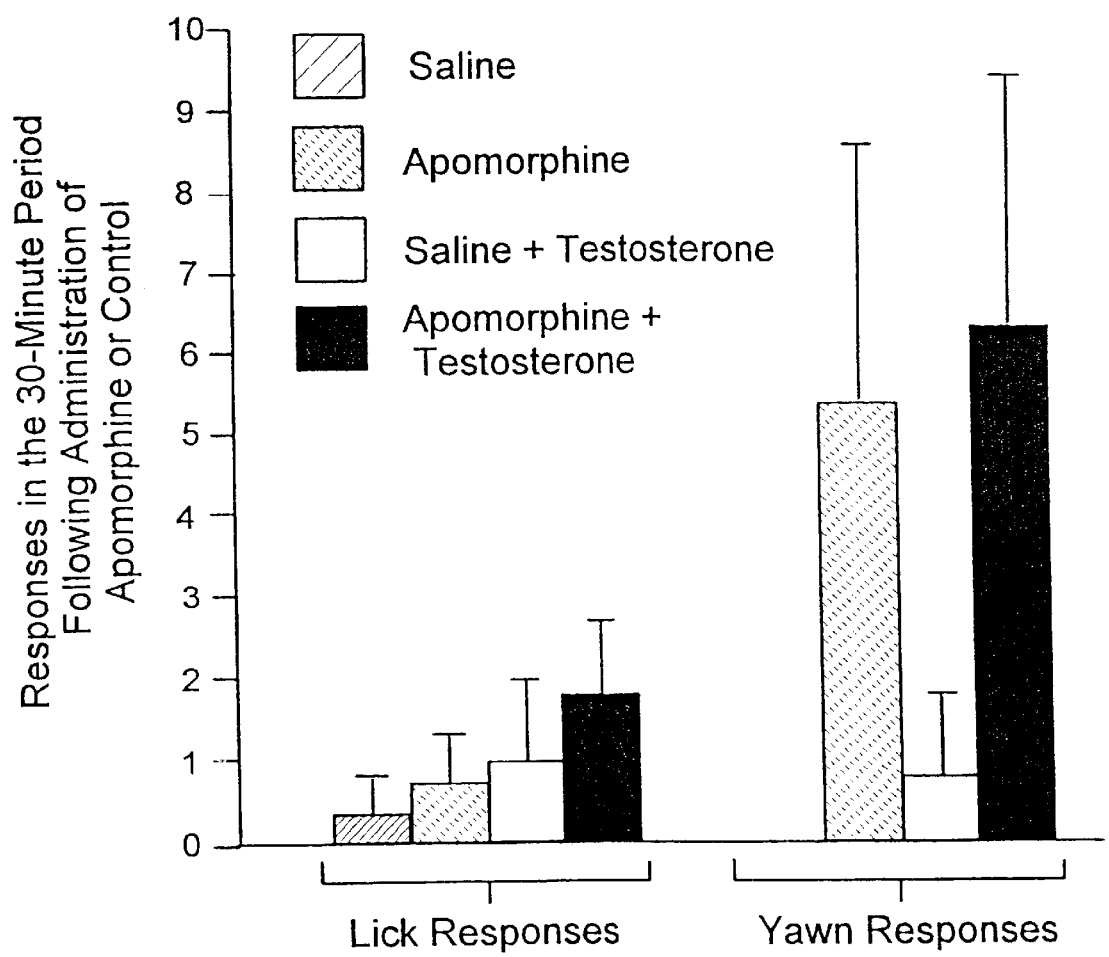
FIG. 8 is a histogram comparing genital lick and yawn response data which compare the data from the studies where either saline or an 80 microgram/kg dose of apomorphine was administered to test animals with and without prior administration of a 480 microgram/kg dose of testosterone.

The genital lick and yawn response data for this experiment are shown graphically in FIG. 8. As can be seen in FIG. 8, the largest number of genital lick responses was seen in ovariectomized animals to which both testosterone and apomorphine had been administered. The effects of apomorphine alone over control or apomorphine in combination with testosterone over control in eliciting yawn responses is dramatic.

This study is informative with regard to the administration of combinations-of testosterone and apomorphine to alleviate sexual dysfunction or normalize sexual function in post-menopausal women or in pre-menopausal women in which the hormonal milieu altered. The altered levels of endogenous hormones in such women are modeled by the ovariectomized rat. The dramatic potentiating influence on the sexual arousal effects of co-administering androgen and apomorphine in the ovariectomized rat strongly suggest the efficacy of the use of this combination in the treatment of post-menopausal women and pre-menopausal women in whom the hormonal milieu is altered. The present invention thus includes the method of inducing effective vasocongestive arousal in such women by co-administering a therapeutically effective dose of apomorphine and an apomorphine-potentiating effective amount of androgen.

Figure 9:
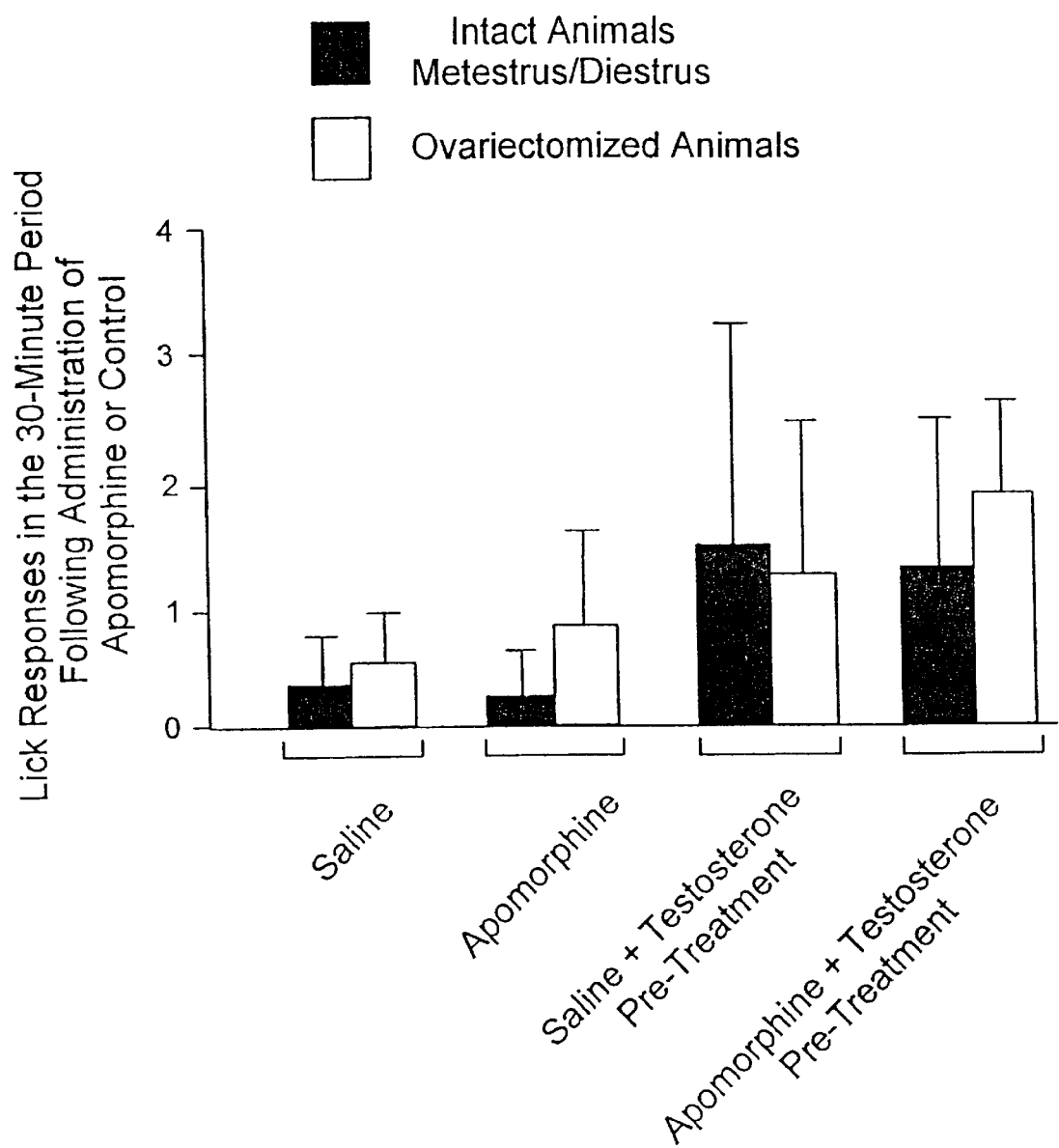
FIGS. 9 and 10 are histograms presenting genital lick and yawn response data, respectively, comparing intact animals administered control or saline during the metestrus/diestrus stage of the rat estrous cycle with ovariectomized animals administered a corresponding regimen of drug or control.

FIG. 9 depicts graphically a comparison of data for intact animals administered apomorphine (with and without testosterone pre-treatment) to ovariectomized animals administered apomorphine (with and without testosterone pre-treatment). The data for the intact animals is shown for the metestrus/diestrus stages, since it is during these stages of the estrus cycle that endogenous hormonal levels are lowest in the intact animals, making for a fairer comparison with ovariectomized animals. As can be seen from FIG. 9, there was no significant difference in genital lick responses between ovariectomized and intact animals, with the exception that in the trial where the animals were administered apomorphine alone.

Figure 10:
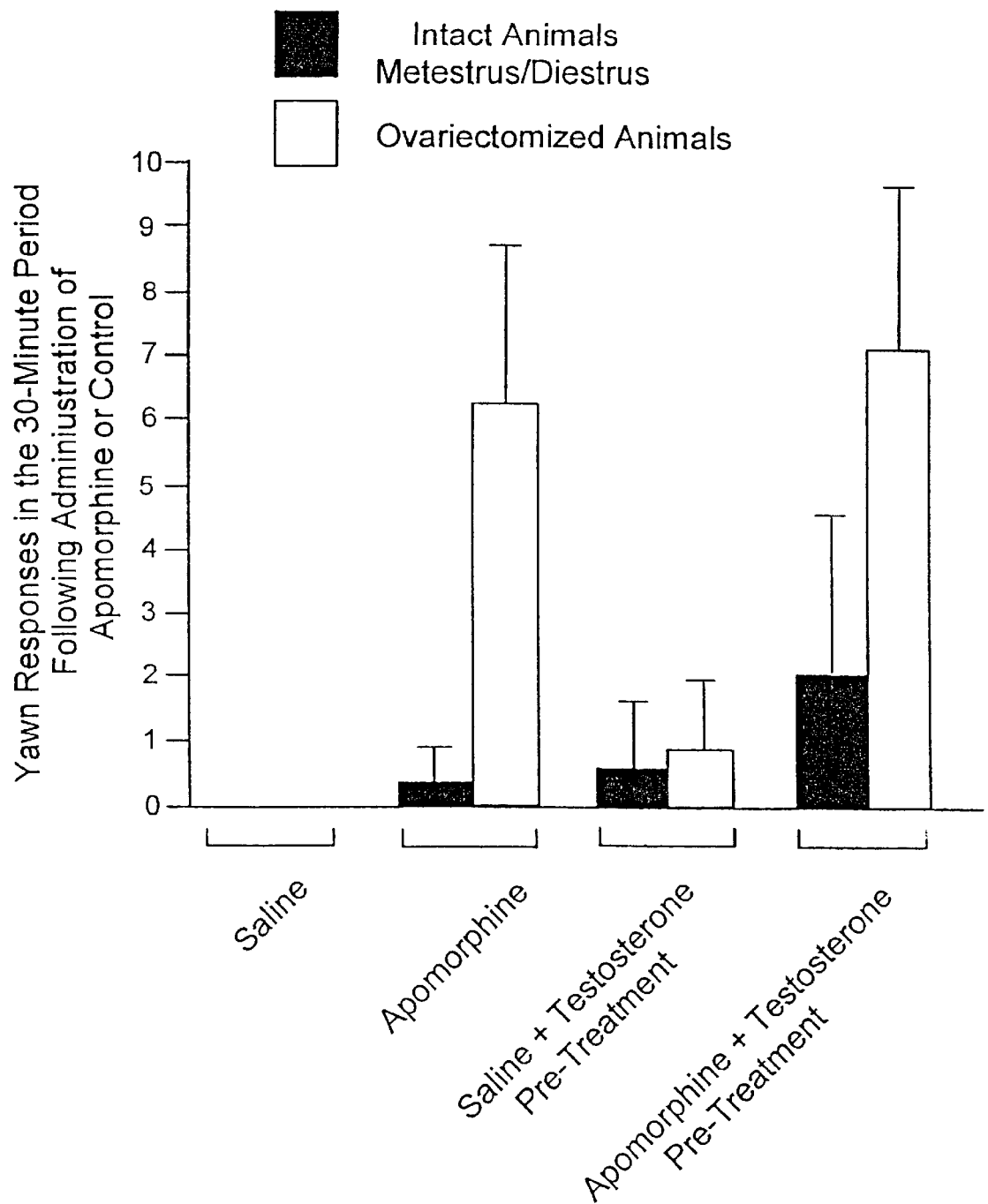

FIG. 10 depicts graphically the corresponding yawn response data comparing the intact and ovariectomized animals. The foregoing data show a marked increase in the apomorphine-treated ovariectomized animals compared with intact animals. The same marked difference in yawn responses in seen in the testosterone- and apomorphine-treated animals.

The foregoing data indicate that apomorphine is effective in initiating a sexual response in female rats. Moreover, the studies show that this sexual response is highly dependent upon hormonal levels of estrogen, progesterone and testosterone, with estrogen and testosterone having a potentiating influence on the effect of apomorphine and progesterone having an inhibitory influence.

The foregoing discussion and the reported studies are intended as illustrative of the present invention and are not to be read as limiting the invention as it is defined by the appended claims.

We claim:

1. A method of treating sexual dysfunction in an ovariectomized female mammal having an altered hormonal milieu, comprising administering to said female apomorphine or a pharmaceutically acceptable salt, ester, or pro-drug thereof, such that sexual dysfunction is treated.

2. The method of claim 1, wherein said altered hormonal milieu is associated with a diminished level of at least one endogenous hormone.

3. The method of claim 1, wherein said female mammal is human.

4. The method of claim 1, wherein said apomorphine is chronically administered.

5. The method of claim 1, wherein said apomorphine is administered on an as-needed basis.

6. The method of claim 1 wherein said apomorphine is administered prior to sexual activity.

7. The method of claim 6 wherein said apomorphine is administered from about 2 minutes to about 120 minutes prior to sexual activity.

8. The method of claim 6 wherein said apomorphine is administered from about 2 minutes to about 60 minutes prior to sexual activity.

9. The method of claim 1 wherein said apomorphine is administered via a route selected from sub-cutaneous, intramuscular, transdermal, sublingual, buccal, intra-nasal, vaginal, and rectal.

10. The method of claim 1 wherein said apomorphine is administered sublingually.

11. The method of claim 1 wherein said apomorphine is administered transdermally.

12. The method of claim 1 wherein said apomorphine is administered intra-nasally.

13. The method of claim 1 wherein said apomorphine or pharmaceutically acceptable salt, ester, or prodrug thereof is administered in an amount between about 1 milligram and about 12 milligrams.

14. The method of claim 1 wherein said apomorphine or pharmaceutically acceptable salt, ester, or prodrug thereof is administered in an amount between about 2.5 milligrams and about 10 milligrams.

15. The method of claim 1 wherein said apomorphine or pharmaceutically acceptable salt, ester, or prodrug thereof is administered in an amount between about 10 and about 100 micrograms per kilogram of body weight.

16. The method of claim wherein said apomorphine or pharmaceutically acceptable salt, ester, or prodrug thereof is administered in an amount between about 25 and about 80 micrograms per kilogram of body weight.

17. The method of claim 1 wherein the plasma concentration of apomorphine is maintained in the range of about 0.3 to about 6 nanograms per milliliter during sexual activity.

18. The method of claim 1 wherein the plasma concentration of apomorphine is maintained in the range of about 0.3 to about 4 nanograms per milliliter during sexual activity.

19. The method of claim 1 wherein the plasma concentration of apomorphine is maintained in the range of about 1 to about 2 nanograms per milliliter during sexual activity.

* * * * *